United States Patent [19]

Smirnov et al.

[11] 3,949,011

[45] Apr. 6, 1976

[54] METHOD OF PREPARING CYCLOOLEFINES

[76] Inventors: Viktor Sergeevich Smirnov, Kutuzovsky prospekt, 26, kv. 555; Vladimir Mikahilovich Gryaznov, Moskovsky Gosudarstvenny Universitet, korpus "L", kv. 11; Margarita Meerovna Ermilova, B.Cherkizovskaya ulitsa, 6, korpus 3, kv. 103; Natalya Vsevolodovna Orekhova, ulitsa M.Ulyanovoi, 9, korpus 1, kv. 95, all of Moscow, U.S.S.R.

[22] Filed: July 1, 1974

[21] Appl. No.: 484,578

[52] U.S. Cl............. 260/666 A; 260/667; 260/683.9; 208/143
[51] Int. Cl.²............................................. C07C 5/16
[58] Field of Search............. 260/666 A, 683.9, 667; 208/143

[56] References Cited
UNITED STATES PATENTS

| | | |
|---|---|---|
| 3,290,406 | 12/1966 | Pfefferle .......................... 260/683.3 |
| 3,344,582 | 10/1967 | Merrill et al..................... 260/666 A |
| 3,360,577 | 12/1967 | Pickles............................. 260/666 A |
| 3,369,052 | 2/1968 | Howell et al..................... 260/666 A |
| 3,408,415 | 10/1968 | Dovell et al. .................... 260/666 A |
| 3,562,346 | 2/1971 | Smirnov et al................... 260/673.5 |
| 3,595,932 | 7/1971 | Moslyansky et al. ............... 260/672 |

*Primary Examiner*—C. Davis
*Attorney, Agent, or Firm*—Steinberg & Blake

[57] ABSTRACT

The method of preparing cycloolefines consists in that, according to the invention, the corresponding cyclodienes are hydrogenated with hydrogen in the presence of a catalyst which is an alloy of palladium with ruthenium or rhodium, the ruthenium content of the alloy being from 1 to 11 per cent (preferably 10 per cent) by weight, and the rhodium content being from 1 to 5 per cent (preferably 2 per cent) by weight, respectively. The hydrogenation is carried out at temperatures from room temperature to 220°C, at a pressure from 1 to 1.5 atm.

10 Claims, No Drawings

METHOD OF PREPARING CYCLOOLEFINES

The invention relates to catalytic processing of petroleum, and more particularly to methods of preparing cycloolefines from cyclic hydrocarbons with two double bonds (cyclodienes).

The method can be used in petrochemical industry for preparing monomers. Rubbers on the basis of cycloolefines are similar to natural rubbers with respect to their properties, they have low vitrification point, which makes it possible to use them under rigorous climatic conditions. The proposed method of preparing cycloolefines can be used for purifying petroleum products from hydrocarbons with conjugated double bonds.

Advantages of methods for preparing cycloolefines are determined by their selectivity, and in particular, by purity of the obtained cycloolefines with respect to the presence of cyclodiene admixtures in them. The difficulty in carrying out the process consist in the necessity of complete conversion during hydrogenation of only one double bond.

Known in the prior art are methods of preparing cycloolefines by hydrogenation of cyclodienes on catalysts which are mostly skeletal metals or metals supported on carriers.

Hydrogenation of cyclodienes in ethyl alcohol solution on a skeletal nickel at 70–80 atm and room temperature yields about 70 percent of cycloolefines (Plate, A. F., Stanko, V. I., Izv. AN USSR, Chemical Science Dept., No. 9, 1148, 1956).

The selectivity of hydrogenation of cyclodienes in the presence of nickel increases in the presence of pyridine (Freudlin, L. K., Polkovnikov, B. D., Izv. AN USSR, Chemical Science Dept., No. 12, 1502, 1956).

Hydrogenation of cyclopentadiene with nickel sulphide on a carrier at temperatures from 275° to 290°C and hydrogen pressure from 5 to 12 atm yields 93.5 percent by volume of cyclopentene, 5.8 percent by volume of cyclopentane, and 0.7 percent by volume of cyclopentadiene remains untreated (U.S. Pat. No. 3,598,877). Hydrogenation of cyclic dienes on a nickel catalyst supported on a carrier pre-treated with thiophene and carbon disulphide, in an autoclave at a temperature of 200°C and a pressure of 35 kg/sq. cm., yields up to 91 percent by volume of cycloolefine and 9 percent by volume of cycloparaffine (U.S. Pat. No. 3,493,625). Hydrogenation of cyclopentadiene on a palladium catalyst supported on calcium carbonate and pre-treated with lead acetate and quinoline yields 85 percent by volume of cyclopentene and 15 percent by volume of cyclopentane (Kuguchev, E. E., Alekseeva, A. V., Neftekhimia, 10, No. 5, 778, 1970). Hydrogenation on a palladium catalyst ($Pd/Al_2O_3$) in the presence of a primary amine at temperatures from −50° to +80°C and at pressures from 14 to 105 kg/sq. cm. gives cyclododecene (from cyclododecadiene) at higher selectivity of the process (U.S. Pat. No. 3,433,842).

Disadvantages of the above-mentioned methods are high pressures, loss of catalyst metal due to attribution of the catalyst during the process, and also contamination of the reaction products with pyridine, quinoline, sulphur, and other substances that are used to treat the catalyst for the purpose of increasing its selectivity. The loss of sulphur compounds during operation of the catalyst decreases its selectivity and shortens its active service. The catalyst therefore requires periodic processing with the above-named substances.

The object of this invention is to provide a method for hydrogenation of cyclodiene hydrocarbons, that would make it possible to carry out the process at maximum selectivity and full conversion of the starting substance.

This object has been attained in a proposed method of preparing cycloolefines, which consists in that the corresponding cyclodienes are hydrogenated with hydrogen in the presence of a catalyst which is an alloy of palladium with ruthenium, or an alloy of palladium with rhodium, the ruthenium content of the alloy being 1–11 percent by weight, and the rhodium content of the alloy being 1–5 percent by weight, at temperatures from room temperature to 220°C and pressures from 1 to 1.5 atm.

The proposed method makes it possible to prepare cycloolefines containing 5, 6 or 8 carbon atoms.

These olefines are valuable monomers for preparing synthetic rubber which is not inferior to natural rubber in its properties. The method can be used for preparing cycloolefines having another number of carbon atoms in the cycle of hydrogenation of the corresponding cyclodienes. According to the invention, cyclopentadiene is hydrogenated to cyclopentene, and cyclooctadiene to cyclooctene.

According to the invention, hydrogenation is carried out in the presence of a catalyst which is an alloy of palladium and ruthenium containing from 1 to 11 percent by weight of ruthenium, or an alloy of palladium with rhodium, containing rhodium in the quantity from 1 to 5 percent by weight.

Palladium is known to be an active catalyst for hydrogenation. Metallic palladium, however, becomes brittle in hydrogen atmosphere. In order to improve catalyst stability towards the action of hydrogen, palladium is alloyed with ruthenium and rhodium. These alloys possess high catalytic activity with respect to the selective hydrogenation of diene hydrocarbons, are stable in hydrogen atmosphere, and are more permeable for hydrogen than pure palladium.

According to the invention, it is advisable to use an alloy of palladium with ruthenium containing 10 ± 0.5 percent of ruthenium. This composition of the catalyst ensures optimum combination of hydrogen permeability for hydrogen and catalytic activity. The above specified accuracy of the ruthenium share in the alloy (±0.5 percent by weight) is connected with specificity of the process for preparing this alloy. Changes in the composition of the alloy within these limits does not affect the catalytic activity of the alloy.

An increase in the content of ruthenium in the alloy above 11 wt. percent leads to a sharp drop of the permeability for hydrogen. This hinders the use of the catalyst in processes of selective hydrogenation of cyclodienes. A decrease of the content of ruthenium in the alloy below 1 wt. percent impairs the strength characteristics of the alloy making it in this respect close to palladium; moreover, the alloy is less stable to the atmosphere of hydrogen and hydrocarbon vapours.

It is recommended to use a catalyst which is an alloy of palladium with rhodium, in which the rhodium content is 2 percent by weight.

A decrease in the content of rhodium below 1 wt. percent leads to the same adverse results as in the case of the palladium-ruthenium alloy, and an increase of the content of rhodium above 5 wt. percent lowers the rate of hydrogen diffusion.

According to the invention, hydrogenation of cyclodiene hydrocarbons is effected at temperatures within the range from 20° to 220°C. Conversion of the starting hydrocarbon increases with temperature, while the selectivity decreases. At lower temperatures (20°–60°C), with the use of hydrogen as a carrier gas, it is possible to obtain cycloolefines under the pass-through conditions at a 100 percent conversion and at almost 100 percent selectivity. If hydrogen is passed by diffusion through a membrane catalyst at temperatures from 60° to 220°C, it is possible, by varying the space feed rate of the carrier gas and the partial pressure of the starting hydrocarbon, to prepare cycloolefine at the selectivity of 0.92 percent and with full conversion of the cyclodiene.

According to the invention, said catalyst can be made in the form of foil, wire, fine tubes or of some other shapes.

According to the invention, a preferred embodiment of the method is one in which hydrogenation is effected on a catalyst made as a membrane, with hydrogen diffusing therethrough. Alloys of palladium with ruthenium or rhodium are selectively permeable for hydrogen only, which makes it possible to realize the process of hydrogenation with hydrogen delivered through a membrane made of these alloys of diffusion. In such an embodiment of the process of cyclodiene hydrogenation the process is carried out selectively to cycloolefines, with a very accurate variation of the quantity of hydrogen passed through the catalyst, which makes incomplete hydrogenation of cyclodienes possible. This can be made by changing the temperature, partial pressure of the delivered hydrocarbon and thickness of the membrane.

The proposed method makes it possible to carry out the hydrogenation process by passing the starting hydrocarbon both per se and in a current of a carrier gas, such as nitrogen, argon, or helium.

The proposed method ensures selective hydrogenation of cyclic hydrocarbons with two double bonds. High selectivity of the process at full conversion is thus assured. In contrast to the known methods, in which the obtained cycloolefines are contaminated with thiophene or carbon disulphide (that increase the selectivity of the catalyst) and hence require an additional purification before further polymerization, the proposed method makes it possible to prevent contamination of the obtained cycloolefine with these comtaminants, and hence the step of additional purification of the catalyst is avoided. The use of a catalyst made of an alloy of palladium with ruthenium or rhodium also prevents catalyst loss in the process. Other advantages of the membrane-type catalyst which is only permeable to hydrogen is that it can be used for hydrogenation of cyclodienes with hydrogen which is prepared by any reaction on the other side of the same catalyst.

The optimum version of the embodiment of the proposed method of hydrogenation of cyclodiene hydrocarbons is the hydrogenation under pass-through conditions on a membrane-type catalyst made as a palladium-ruthenium foil, containing 10 percent by weight of ruthenium, the membrane dividing the reaction vessel into two chambers. Cyclodiene vapour in a mixture with an inert gas is passed at a space flow rate of 5–15 mole/sq. m. of the catalyst surface per hour through one chamber of the reactor and a mixture of hydrogen with an inert gas is passed through the other chamber, the partial pressure of hydrogen in the mixture being from 0.2 to 1.5 atm.

The temperature of the process is from 60° to 220°C. By regulating the temperature of the reactor, the partial pressure of hydrogen and of hydrocarbon, it is possible to carry out the process selectively at practically full conversion of the starting cyclodiene.

For a better understanding of the invention, the following examples of its practical embodiment are given by way of illustration.

(The products were analyzed by gas-partition chromatography).

EXAMPLE 1

The catalyst is 3.93 g of an alloy of palladium with ruthenium containing 4.36 percent by weight of ruthenium. The catalyst, in the form of fine chips, is loaded into a quartz reaction vessel, and hydrogen is passed at a pressure of 1 atm at a space rate of feed of 33 ml/min. A mixture of cyclopentadiene vapour with helium is admitted into the reaction vessel through a gas-cock in 0.2 ml portions (with respect to cyclopentadiene).

The dependence of the catalysate composition on the reaction temperature is illustrated in Table 1.

Table 1.

| Nos | Temperature, °C | Catalysate composition,%(v/v) | | | Conversion in % | Selectivity |
| --- | --- | --- | --- | --- | --- | --- |
|  |  | cyclopentadiene | cyclopentene | cyclopentane |  |  |
| 1 | 27 | 76.6 | 20.4 | — | 20.4 | 1.0 |
| 2 | 34 | 73.0 | 27.0 | — | 27.0 | 1.0 |
| 3 | 35 | 72.2 | 27.8 | — | 27.8 | 1.0 |
| 4 | 44 | 67.1 | 32.9 | — | 32.9 | 1.0 |
| 5 | 47 | 62.2 | 37.8 | — | 37.8 | 1.0 |
| 6 | 56 | 55.6 | 46.4 | — | 46.4 | 1.0 |
| 7 | 67 | 36.0 | 63.3 | 0.7 | 64.0 | 0.99 |
| 8 | 75 | 13.3 | 83.0 | 3.7 | 86.7 | 0.96 |
| 9 | 84 | 1.2 | 92.5 | 6.3 | 98.8 | 0.9 |
| 10 | 92 | — | 91.7 | 8.3 | 100 | 0.92 |
| 11 | 102 | — | 85.7 | 14.3 | 100 | 0.86 |
| 12 | 122 | — | 70.5 | 29.5 | 100 | 0.71 |

As the temperature increases from 27° to 84°C the yield of cyclopentene increases to 92.5 percent.

The product of full hydrogenation, cyclopentane, appears only at a temperatures above 60°C. At temperatures from 84 to 92°C, and at atmospheric pressure of hydrogen, the selectivity of preparing cyclopentene is 0.93, and at lower temperatures the selectivity is practically absolute.

EXAMPLE 2

The catalyst is 3.93 g of foil, 0.1 mm thick, made of an alloy of palladium containing 4.36 percent by weight of ruthenium.

Into a current of hydrogen at a pressure of 1.2 atm., which passes through the reactor at a space flow rate of 60 ml/min., introduced by pulses are 0.001 ml portions of 1,5-cyclooctadiene. The dependence of the catalysate composition on the temperature is shown in Table 2.

Table 2.

| Nos | Temperature, °C | Composition of catalysate,% (v/v) | | | Conversion in % | Selectivity |
| --- | --- | --- | --- | --- | --- | --- |
| | | cyclooctane | cyclooctene | cyclooctadiene | | |
| 1 | 30 | 0.3 | 99.7 | — | 100 | 0.99 |
| 2 | 37 | 17.0 | 83.0 | — | 100 | 0.83 |
| 3 | 53 | 46.1 | 53.9 | — | 100 | 0.54 |
| 4 | 66 | 99.7 | — | 0.3 | 99.7 | 0 |

The Table shows that the selectivity of the process, with respect to cycloolefine, at a temperature of 30°C, is close to to unity.

EXAMPLE 3

The catalyst is an alloy of palladium containing 2 percent by weight of ruthenium, made in the form of foil. The foil (2.13 g) is cut into strips and placed into a pass-through reactor made of stainless steel. The hydrogenation reaction is carried out in an atmosphere of hydrogen at atmospheric pressure and at a space rate of its flow of 40 ml/min. Cyclopentadiene is passed at a temperature of 61°C and at a space flow rate of 0.57 mole/sq. m. per hour, its conversion under these conditions attaining 75.1 percent, at the selectivity of 0.72.

EXAMPLE 4

The catalyst is an alloy of palladium containing 9.78 percent by weight of ruthenium. A foil, 0.1 mm thick, weighing 1.9 g and having the visible surface of 18 sq. cm., divides the reaction vessel into two chambers. Cyclopentadiene vapour is delivered into one chamber at a space flow rate of 7 mole/sq. m. per hour in a mixture with argon. Hydrogen is supplied into the other chamber at a space flow rate of 40 ml/min. Hydrogen penetrates the membrane and enters the reaction with cyclopentadiene on its other side. At a temperature of 106°C, a catalysate is obtained containing 92.0 percent by volume of cyclopentene and 8 percent by volume of cyclopentane.

EXAMPLE 5

The catalyst is a foil of an alloy of palladium with ruthenium containing 10.3 percent by weight of ruthenium. The thickness of the foil is 0.1 mm, the visible surface is 18 sq. cm. The hydrogenation of cyclopentadiene is carried out in the reactor described in Example 4, with delivery of cyclopentadiene at a space flow rate of 1.0 mole/sq. m. per hour in a current of nitrogen. The depth of conversion at a temperature of 219°C is 68 percent at a selectivity of 0.99. The catalysate contains 67.3 percent of cyclopentene, 0.7 percent of cyclopentane, and 32 percent of non-reacted cyclopentadiene.

EXAMPLE 6

The catalyst is an alloy of palladium containing 5 percent by weight of rhodium. Fine chips of the catalyst (3.28 g) are loaded into a quartz reactor and hydrogen is passed at a pressure of 1.0 atm at a rate of 60 m/minute. A mixture of cyclopentadiene vapour with helium is introduced into the reactor by portions of 0.2 ml of cyclopentadiene.

The dependence of the catalysate composition on the temperature of the process is shown in Table 3.

Table 3.

| Nos | Temperature, °C | Catalysate composition,%(v/v) | | | Conversion in % | Selectivity |
| --- | --- | --- | --- | --- | --- | --- |
| | | cyclopentadiene | cyclopentene | cyclopentane | | |
| 1 | 105 | 95.8 | 4.2 | — | 4.2 | 1.0 |
| 2 | 128 | 94.3 | 5.7 | — | 5.7 | 1.0 |
| 3 | 150 | 80.4 | 19.6 | — | 19.6 | 1.0 |
| 4 | 152 | 78.4 | 21.2 | 0.4 | 21.6 | 0.98 |
| 5 | 170 | 74.4 | 25.0 | 0.6 | 25.6 | 0.98 |
| 6 | 175 | 61.1 | 38.2 | 0.7 | 38.9 | 0.98 |
| 7 | 200 | 58.5 | 31.1 | 0.4 | 41.5 | 0.99 |
| 8 | 213 | 44.9 | 53.7 | 1.4 | 55.1 | 0.97 |
| 9 | 238 | 28.4 | 69.0 | 2.6 | 71.6 | 0.96 |

Table 3 shows that the degree of conversion increases with increase of temperature.

EXAMPLE 7

The catalyst is an alloy of palladium with rhodium, containing 2.0 percent by weight of rhodium, made in the form of a 0.1 mm thick foil. The reaction is carried out in the reactor described in Example 4 with a membrane made of the catalyst foil and having the visible surface of 18 sq. cm. Cyclopentadiene is hydrogenated at a space flow rate of 5 mole/hour per sq. m. of the catalyst in a current of argon. The conversion at a temperature of 200°C is complete and the selectivity with respect to cyclopentene is 0.87.

We claim:

1. Method of selectively hydrogenating a cyclodiene into the corresponding cyclic mono-olefine, which comprises subjecting said cyclodiene to hydrogenation with hydrogen in the presence of a catalyst selected from the group consisting of alloys of 1 to 11 percent by weight ruthenium with the balance palladium and alloys of 1 to 5 percent by weight rhodium with the balance palladium, at temperatures from room temperature to 220°C and at a pressure from 1 to 1.5 atm.

2. A method according to claim 1, in which cyclopentadiene is hydrogenated to cyclopentene.

3. A method according to claim 1, in which cyclooctadiene is hydrogenated to cyclooctene.

4. A method according to claim 1, in which the catalyst is an alloy of palladium with ruthenium containing 10 percent by weight of ruthenium and the balance palladium.

5. A method according to claim 1, in which the catalyst is an alloy of palladium with rhodium containing 2 percent by weight of rhodium and the balance palladium.

6. A method according to claim 1, in which said catalyst is in the form of wire.

7. A method according to claim 1, in which said catalyst is in the form of foil.

8. A method according to claim 1, in which said catalyst is in the form of fine-walled tubes.

9. A method according to claim 1, in which the hydrogenation process is carried out on said catalyst made as a membrane through which hydrogenation is diffused.

10. A method according to claim 1, in which said cyclodiene in admixture with an inert gas selected from the group consisting of nitrogen, argon, and helium is subjected to hydrogenation.

* * * * *